United States Patent [19]

Hall

[11] Patent Number: 4,838,927
[45] Date of Patent: Jun. 13, 1989

[54] DIVALENT METAL SALTS IMPROVE COMPOSITIONS OF ASYMMETRICAL TRIAZINE MIXTURES

[75] Inventor: William T. Hall, Wilmington, Del.

[73] Assignee: E. I. Du Pont de Nemours and Company, Wilmington, Del.

[21] Appl. No.: 938,613

[22] Filed: Dec. 5, 1986

[51] Int. Cl.$^4$ .............................................. A01 25/22
[52] U.S. Cl. ...................................................... 71/93
[58] Field of Search ............................................ 71/93

[56] References Cited

U.S. PATENT DOCUMENTS 3,905,801 9/1975 Fawzi ..................................... 71/93

FOREIGN PATENT DOCUMENTS 1049805 3/1979 Canada .

OTHER PUBLICATIONS

Directions for Use with "Lexone".

Primary Examiner—Catherine L. Mills

[57] ABSTRACT

Asymmetrical triazines form stable tank mixtures with trifluralin in the presence of an effective amount of a suitable divalent metal salt.

7 Claims, No Drawings

DIVALENT METAL SALTS IMPROVE COMPOSITIONS OF ASYMMETRICAL TRIAZINE MIXTURES

BACKGROUND OF THE INVENTION

This invention relates to improved asymmetric triazine composition, which are useful as agricultural chemicals and in particular as herbicides, both general and selective.

In U.S. Pat. No. 4,036,632 compounds of the general formula are disclosed.

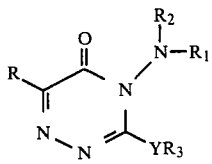

In the above formula R may be alkyl of $C_1$–$C_{18}$ carbon atoms, $R_1$ and $R_2$ may be hydrogen, Y may be O, S, or $NR_4$; wherein R may be hydrogen or alkyl of $C_1$–$C_{18}$ carbon atoms and $R_3$ may be the same.

Although the compounds named in the U.S. Pat. No. 4,036,632 patent include outstanding herbicides, a need still exists for additional formulations which have even better properties such as handling characteristics. There is a need for compounds which form stable liquid slurries that are compatible with other herbicides. The need for such stability is readily apparent; often formuations of herbicides have to be stored in mixing tanks from which the material is applied to vegetation. Anything which accelerates the settling out of the formulation, while in storage will, or course, result in there being less active ingredient for the purpose intended, i.e., herbicidal utility. The sedimentation can also lead to clogged application equipment, especially spray nozzles. It is also often important to use combinations of herbicides since one herbicide normally will not control all of the undesired weed species. Generally, complementary herbicides are tank mixed to get broad spectrum control. Thus, a herbicide which is readily compatible with other herbicides has a distinct advantage over herbicides that are not as compatible with other herbicides.

SUMMARY OF THE INVENTION

This invention pertains to novel formulations containing (1) mixtures of either 4-amino-6-(1,1-dimethylethyl)-3-ethylthio-1,2,4-triazin-5(4H)-one (ethyl metribuzin) or 4-amino-6-(1,1-dimethylethyl)-3-methylthio-1,2,4-triazin-5(4H)-one (metribuzin), (2) a monovalent cation, such as a sodium, (3) an agriculturally useful formulation of trifluralin $\alpha,\alpha,\alpha$-trifluoro-2,6-dinitro-N,N-dipropyl-p-toluidine in a liquid medium which is preferably aqueous and produces a mixture with (1), is subject to particle growth of metribuzin or ethyl metribuzin and (4) an agriculturally suitable divalent metal salt such as a calcium salt, in an amount effective to retard the previously mentioned growth of metribuzin particles in the mixture.

DETAILED DESCRIPTION OF THE INVENTION

According to this invention it has been unexpectedly found that addition of soluble divalent metal cations, customarily abbreviated $M^{2+}$, to either an ethyl metribuzin or metribuzin/trifluralin tank mix will inhibit metribuzin or ethyl metribuzin particle growth. The preferred $M^{2+}$ cation is calcium, but magnesium, zinc and others are also effective. Typically, they may be added as the following salts, chloride, nitrate, sulfate, ligninsulfonate, alkylarylsulfonate, or dodecylbenzenesulfonate.

Furthermore the amount of $M^{2+}$ needed to inhibit particle growth is proportional to the amount of monovalent cations ($M^{1+}$) introduced into solution as part of the formulation(s). Examples of $M^{1+}$ are sodium, potassium, lithium and ammonium.

It is common to formulate metribuzin products with anionic surfactants containing $M^{1+}$ counter ions. Typical counter ions are ligninsulfonate, alkyarylsulfonates, alkylsulfosuccinates and methyl taurates. Particularly prevalent are sodium derivatives. Thus as a consequence of dispersing the metribuzin product in the spray tank solution, $M^{1+}$ is introduced from the dissolution of the anionic surfactant(s). As currently practiced, the amount of $M^{2+}$ is present in commercial formulations of metribuzin is negligible. Metribuzin particle growth proceeds rapidly when trifluralin is admixed.

By introducing $M^{2+}$ into a metribuzin-trifluralin mixture so as to adjust the mole ratio of $M^{1+}/M^{2+}$ in solution to less than 2.5, metribuzin particle growth is inhibited. The $M^{1+}/M^{2+}$ ratio can be adjusted in a number of ways as described. It is required that $M^{1+}$ and $M^{2+}$ are soluble species.

It is possible to inhibit particle growth by adding the required amount of $M^{2+}$, as a water-soluble salt, to the solution prior to the addition of metribuzin and trifluralin. Although effective, this procedure has the disadvantage of adding an extra step during the preparation of the spray tank mixture. It is preferable to build the proper $M^{1+}/M^{2+}$ ratio into the product formulation so no extra handling is required. Since $M^{1+}$ is introduced almost entirely as part of the metribuzin formulation ingredients, it is appropriate to adjust the $M^{1+}/M^{2+}$ ratio in that product. Alternatively, $M^{2+}$ could be added to the trifluraline so that, when combined with metribuzin, the desired $M^{1+}/M^{2+}$ ratio is obtained.

One method to adjust $M^{1+}/M^{2+}$ in the metribuzin product is to incorporate the required amount of water-soluble $M^{2+}$ salt into the current formulation. For this purpose $CaSO_4$ is particularly useful, $ZnSO_4$ and $MgSO_4$ are also acceptable. The anion portion of the salt is unrestricted, so long as it is agriculturally acceptable and renders the salt water-soluble. Acceptable anions include halides, sulfates or nitrates.

Another method for adjusting the $M^{1+}/M^{2+}$ ratio in the metribuzin product is to replace $M^{1+}$ derivatives of anionic surfactants with $M^{2+}$ derivatives. For example, it is common to use a sodium ligninsulfonate, and this could be replaced by a calcium ligninsulfonate. Not all of the $M^{1+}$ must be replaced with $M^{2+}$, only enough to meet $M^{1+}/M^{2+}$ requirement.

Although the use of $M^{2+}$ surfactants in metribuzin formulations has been recognized in a general way in a prior patent, U.S. Pat. No. 4,036,632, the relationship of $M^{1+}/M^{2+}$ and its effect on metribuzin particle growth was not taught nor was the acceptable ratio.

A method for adjusting $M^{1+}/M^{2+}$ through alteration of the trifluralin product is to add a soluble $M^{2+}$ species to the concentrate. A particularly useful material for this purpose is calcium dodecylbenzenesulfonate.

EXAMPLE 1

An example of a representative solid metribuzin formulation is given in Composition I.

| Composition I | |
|---|---|
| Ingredient | Wt. % |
| Metribuzin | 75.0 |
| Technical Impurities | 5.6 |
| Reax ® 45T | 7.0 |
| Petro ® Dispersant 98 | 2.0 |
| Kaolin Clay | 10.4 |

The components are blended together and pulverized until substantially all the particles are less than 50 microns. The resulting powder disperses readily in water.

The surfactants used in this example, Reax ® 45T and Petro ® Dispersant 98, are sodium derivatives of anionic surfactants of a type commonly used in solid agricultural formulations. Reax ® 45T (Westvaaco) is a blend of anionic wetting agents combined with a ligninsulfonate dispersant. Petro ® Dispersant 98 (Petrochemicals Co.) is a wetting/dispersing agent derived from alkylnaphthalenesulfonate.

EXAMPLE 2

This example demonstrates one method for adjusting $M^{1+}/M^{2+}$ to the proper ratio in a formulation which uses $M^{1+}$ surfactants, like Composition I. Thus to Composition I, the $M^{2+}$ salt is added directly, replacing some of the inert clay. The result is Composition II shown below.

| Composition II | |
|---|---|
| Ingredient | Wt. % |
| Metribuzin | 75.0 |
| Technical Impurities | 5.6 |
| Reax ® 45T | 7.0 |
| Petro ® Dispersant 98 | 2.0 |
| Kaolin Clay | 8.4 |
| $CaSO_4.2H_2O$ | 2.0 |

The components are blended and pulverized in the same way as Example 1

EXAMPLE 3

This example illustrates the removal of sodium surfactant and replacement with a calcium derivative. Thus using I as the standard, the Reax ® 45T is replaced with Daxad 21 (W. R. Grace), a calcium salt of polymerized alkyl arylsulfonic acids.

| Composition III | |
|---|---|
| Ingredient | Wt. % |
| Metribuzin | 75.0 |
| Technical Impurities | 5.6 |
| Daxad ® 21 | 7.0 |
| Petro ® Dispersant 98 | 2.0 |
| Kaolin Clay | 10.4 |

The components are blended and pulverized in the same way as Example 1.

EXAMPLE 4

This example illustrates the addition of a soluble $M^{2+}$ species to the trifluralin formulation so that in combination with a metribuzin formulation like I the required $M^{1+}/M^{2+}$ is obtained. In this case calcium dodecylbenzenesulfonate (Ninate 401, Stepan Chemical Co.) is added to a commercial trifluralin product, Treflan ® (Elanco).

| Composition IV | |
|---|---|
| Ingredient | Wt. % |
| Treflan ® EC | 98 |
| Ninate 401 | 2 |

UTILITY

The utility of the invention is demonstrated by comparing the performance of I, II and III in combination with Treflan ®, a standard commercial trifluralin formulation, and by the combination of I plus IV. The test is designed to simulate conditions that might be found in actual commercial operation. Since most spraying apparatus are equipped with filter screens having apertures of 50 mesh (300 microns) and larger, metribuzin particles must be kept smaller than this in order to be applied without plugging the screens. Therefore of interest in these tests is determining the amount of material retained by a 50 mesh screen after a specified period of time.

The tests are run by dispersing the metribuzin containing powder in dionized water. Treflan ® EC is then mixed in, and the material is allowed to stand for 6 hours. After this time the entire mixture is washed through an ASTM 50 mesh sieve, and any material retained is collected, dried and weighed. The material collected is essentially all metribuzin, so the weight of the retains is divided by the total weight of metribuzin in the mixture to find the percent of the metribuzin greater than 50 mesh. The results are as follows.

| Ingredients in 250 mL $H_2O$ | After 6 hours % Metribuzin + 50 mesh | Mole $M^{1+}$/Mole $M^{2+}$ in Solution |
|---|---|---|
| (Test 1) 1.5 g I + 4.7 mL Treflan ® EC | 18.0 | 4.1 |
| (Test 2) 1.5 g II + 4.7 mL Treflan ® EC | 0.15 | 2.1 |
| (Test 3) 1.5 g III + 4.7 mL Treflan ® EC | <0.1 | 0.6 |
| (Test 4) 1.5 g I + 4.7 mL IV | <0.1 | 1.7 |

The $M^{1+}/M^{2+}$ mole ratio is determined in the following manner. Each sample, I–IV and Treflan ® EC, is analyzed separately for soluble $M^{1+}$ and $M^{2+}$, in this case sodium and calcium. The analysis is performed by: dispersing 1.0 gram of sample in 100 ml of dionized water, filtering the solution, and measuring the cation content in the aqueous phase by standard atomic absorption techniques. From the $M^{1+}$, $M^{2+}$ content of each component, the total $M^{1+}$, $M^{2+}$ content of the mixture is calculated and the result is expressed in terms of the mole ratio $M^{1+}/M^{2+}$.

The benefits of the current invention are evident in tests 1–4. In test 1, where $M^{1+}/M^{2+}$ is greater than 2.5, a relatively major amount of metribuzin is larger than 50 mesh after six hours. In tests 2–4, where $M^{1+}/M^{2+}$ is in the desired range less than 2.5, the amount of metribuzin larger than 50 mesh after six hours is relatively small. It is obvious that use of metribuzin-trifluralin tank mixtures under conditions of tests 2-4 will result in fewer application problems.

The herbicidal mixtures can include additional pesticides. One herbicide which may be included to the mixture is ethyl 2-[[(4-chloro-6-methoxypyrimidin-2-yl)aminocarbonyl]aminosulfonyl]benzoate.

What is claimed is:

1. A herbicidal mixture consisting essentially of a first herbicide selected from the group consisting of 4-amino-6-(1,1-dimethylethyl)-3-ethylthio-1,2,4-triazin-5(4H)-one or 4-amino-6-(1,1-dimethyl)-3-methylthio-1,2,4-triazin-5(4H)-one, a monovalent cation, a second herbicide, α,α,α,-trifluoro-2,6-dinitro-N,N-dipropyl-p-toluidine, in a liquid medium and sufficient amounts of an agriculturally suitable divalent cation, present in such proportions as to retard the formation of crystals of the first herbicide and wherein the mole ratio of the monovalent cation to the divalent cation is less than 2.5.

2. The mixture of claim 1 wherein the liquid medium is an aqueous medium.

3. The mixture of claim 2 wherein the divalent cation is calcium.

4. The mixture of claim 2 wherein the divalent cation is zinc.

5. The mixture of claim 2 wherein the divalent cation is magnesium.

6. The mixture of claim 3 wherein the monovalent salt is sodium.

7. The mixture of claim 2 wherein the first herbicide is 4-amino-6-(1,1-dimethyl)-3-methylthio-1,2,4-triazin-5(4H)-one.

* * * * *